United States Patent
Pacetti et al.

(10) Patent No.: US 9,675,483 B2
(45) Date of Patent: Jun. 13, 2017

(54) PROTECTIVE SHEATH ASSEMBLY FOR A POLYMER SCAFFOLD

(71) Applicant: Abbott Cardiovascular Systems Inc., Santa Clara, CA (US)

(72) Inventors: Stephen D. Pacetti, San Jose, CA (US); Annie P. Liu, Cupertino, CA (US); Mark C. Johnson, Murrieta, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 784 days.

(21) Appl. No.: 13/924,421

(22) Filed: Jun. 21, 2013

(65) Prior Publication Data

US 2014/0379064 A1  Dec. 25, 2014

(51) Int. Cl.
*A61F 2/962* (2013.01)
*A61F 2/958* (2013.01)
(Continued)

(52) U.S. Cl.
CPC ............... *A61F 2/958* (2013.01); *A61F 2/82* (2013.01); *A61F 2/962* (2013.01); *A61L 31/048* (2013.01); *A61L 31/06* (2013.01); *A61L 31/14* (2013.01); *A61L 31/148* (2013.01); *A61F 2/0095* (2013.01); *A61F 2/95* (2013.01); *A61F 2/966* (2013.01); *A61F 2/97* (2013.01); *A61F 2002/9583* (2013.01); *A61F 2210/0004* (2013.01); *A61F 2250/0059* (2013.01)

(58) Field of Classification Search
CPC .. A61F 2/958; A61F 2/82; A61F 2/962; A61F 2/95; A61F 2/966; A61F 2/97; A61F 2/0095; A61F 2002/9583; A61F 2250/0059; A61F 2210/0004; A61L 31/14; A61L 31/06; A61L 31/048; A61L 31/148; A61M 2025/0668; A61M 2025/0675

See application file for complete search history.

(56) References Cited

U.S. PATENT DOCUMENTS

| 4,243,050 | A | 1/1981 | Littleford |
| 4,581,025 | A | 4/1986 | Sheath |

(Continued)

FOREIGN PATENT DOCUMENTS

| WO | WO 98/39056 | 9/1998 |
| WO | WO 02/060345 | 8/2002 |
| WO | WO 2011/094048 | 8/2011 |

OTHER PUBLICATIONS

U.S. Appl. No. 13/644,347, filed Oct. 4, 2012, Wang.
(Continued)

*Primary Examiner* — Melanie Tyson
*Assistant Examiner* — Rachel S Highland
(74) *Attorney, Agent, or Firm* — Squire Patton Boggs (US) LLP

(57) ABSTRACT

A medical device includes a polymer scaffold crimped to a catheter having an expansion balloon. A sheath is placed over the crimped scaffold after crimping to reduce recoil of the crimped polymer scaffold and maintain scaffold-balloon engagement relied on to hold the scaffold to the balloon when the scaffold is being delivered to a target in a body. The sheath is removed by a health professional either by removing the sheath directly or using a tube containing the catheter.

20 Claims, 12 Drawing Sheets

(51) Int. Cl.
    *A61F 2/82*     (2013.01)
    *A61L 31/14*     (2006.01)
    *A61L 31/04*     (2006.01)
    *A61L 31/06*     (2006.01)
    *A61F 2/95*     (2013.01)
    *A61F 2/966*     (2013.01)
    *A61F 2/00*     (2006.01)
    *A61F 2/97*     (2013.01)

(56) References Cited

U.S. PATENT DOCUMENTS

| | | |
|---|---|---|
| 4,710,181 A | 12/1987 | Fuqua |
| 5,015,231 A | 5/1991 | Keith et al. |
| 5,158,545 A | 10/1992 | Trudell et al. |
| 5,211,654 A | 5/1993 | Kaltenbach |
| 5,250,033 A | 10/1993 | Evans et al. |
| 5,352,236 A | 10/1994 | Jung et al. |
| 5,458,615 A | 10/1995 | Klemm et al. |
| 5,545,211 A | 8/1996 | An et al. |
| 5,569,294 A | 10/1996 | Parkola |
| 5,591,226 A | 1/1997 | Trerotola et al. |
| 5,647,857 A | 7/1997 | Anderson et al. |
| 5,653,697 A | 8/1997 | Quiachon et al. |
| 5,693,066 A | 12/1997 | Rupp et al. |
| 5,709,703 A | 1/1998 | Lukic et al. |
| 5,749,852 A | 5/1998 | Schwab et al. |
| 5,765,682 A | 6/1998 | Bley et al. |
| 5,776,141 A | 7/1998 | Klein et al. |
| 5,782,855 A | 7/1998 | Lau et al. |
| 5,817,100 A | 10/1998 | Igaki |
| 5,868,707 A | 2/1999 | Williams et al. |
| 5,893,868 A | 4/1999 | Holman et al. |
| 5,964,730 A | 10/1999 | Williams et al. |
| 6,010,529 A | 1/2000 | Herweck et al. |
| 6,110,146 A | 8/2000 | Berthiaume et al. |
| 6,132,450 A | 10/2000 | Hanson et al. |
| 6,152,944 A | 11/2000 | Holman et al. |
| 6,197,016 B1 | 3/2001 | Fourkas et al. |
| 6,254,609 B1 | 7/2001 | Vrba et al. |
| 6,254,628 B1 | 7/2001 | Wallace et al. |
| 6,334,867 B1 | 1/2002 | Anson |
| 6,342,066 B1 | 1/2002 | Toro et al. |
| 1,355,101 A1 | 3/2002 | Van Muiden |
| 6,416,529 B1 | 7/2002 | Holman et al. |
| 6,447,540 B1 | 9/2002 | Fontaine et al. |
| 6,533,806 B1 | 3/2003 | Sullivan et al. |
| 6,749,584 B2 | 6/2004 | Briggs et al. |
| 6,783,542 B2 | 8/2004 | Eidenschink |
| 6,790,224 B2 | 9/2004 | Gerberding |
| 6,805,703 B2 | 10/2004 | McMorrow |
| 6,827,731 B2 | 12/2004 | Armstrong et al. |
| 6,899,727 B2 | 5/2005 | Armstrong et al. |
| 7,198,636 B2 | 4/2007 | Cully et al. |
| 7,314,481 B2 | 1/2008 | Karpiel |
| 7,347,868 B2 | 3/2008 | Burnett et al. |
| 7,384,426 B2 | 6/2008 | Wallace et al. |
| 7,618,398 B2 | 11/2009 | Holman et al. |
| 7,998,404 B2 | 8/2011 | Huang et al. |
| 8,414,528 B2 | 4/2013 | Liu et al. |
| 8,539,663 B2 | 9/2013 | Wang et al. |
| 8,752,265 B2 | 6/2014 | Wang |
| 2001/0001128 A1 | 5/2001 | Holman et al. |
| 2002/0052640 A1 | 5/2002 | Bigus et al. |
| 2002/0099431 A1 | 7/2002 | Armstrong et al. |
| 2003/0004561 A1 | 1/2003 | Bigus et al. |
| 2003/0212373 A1 | 11/2003 | Hall et al. |
| 2004/0073286 A1 | 4/2004 | Armstrong et al. |
| 2004/0143315 A1 | 7/2004 | Bruunn et al. |
| 2006/0015171 A1 | 1/2006 | Armstrong et al. |
| 2008/0010947 A1 | 1/2008 | Huang et al. |
| 2009/0221965 A1 | 9/2009 | Osypka |
| 2010/0004735 A1 | 1/2010 | Yang et al. |
| 2011/0066222 A1* | 3/2011 | Wang ................. A61F 2/91 623/1.15 |
| 2011/0184509 A1 | 7/2011 | Von Oepen et al. |
| 2012/0042501 A1 | 2/2012 | Wang et al. |
| 2012/0109281 A1 | 5/2012 | Papp |
| 2012/0261858 A1 | 10/2012 | Roberts et al. |
| 2012/0285609 A1 | 11/2012 | Wang |
| 2012/0302955 A1 | 11/2012 | Liu et al. |
| 2012/0324696 A1 | 12/2012 | Liu et al. |
| 2014/0096357 A1 | 4/2014 | Wang |
| 2014/0157567 A1 | 6/2014 | Wang |
| 2014/0379064 A1 | 12/2014 | Pacetti et al. |

OTHER PUBLICATIONS

U.S. Appl. No. 13/708,638, filed Dec. 7, 2012, Wang et al.
U.S. Appl. No. 13/840,257, filed Mar. 15, 2013, Hossainy et al.
Angioplasty Summit Abstracts/Oral, The Am. J. of Cardiology, Apr. 23-26, 2013, p. 23B.
Bosiers et al., "Coronary and endovascular applications of the Absorb™ bioresorbable vascular scaffold", Interv. Cardiol. 4(6), pp. 621-631 (2012).
Miller "Abbott's Bioresorbable Stent Shows Durable Results in ABSORB Trial", The Gray Sheet, pp. 17-18, Mar. 2003.
International Search Report and Written Opinion for PCT/US2014/041972 mailed Nov. 28, 2014, 13 pgs.
Office Action mailed Dec. 2, 2016 in Chinese Patent Application No. 201480035416.5, 12 pages.

* cited by examiner

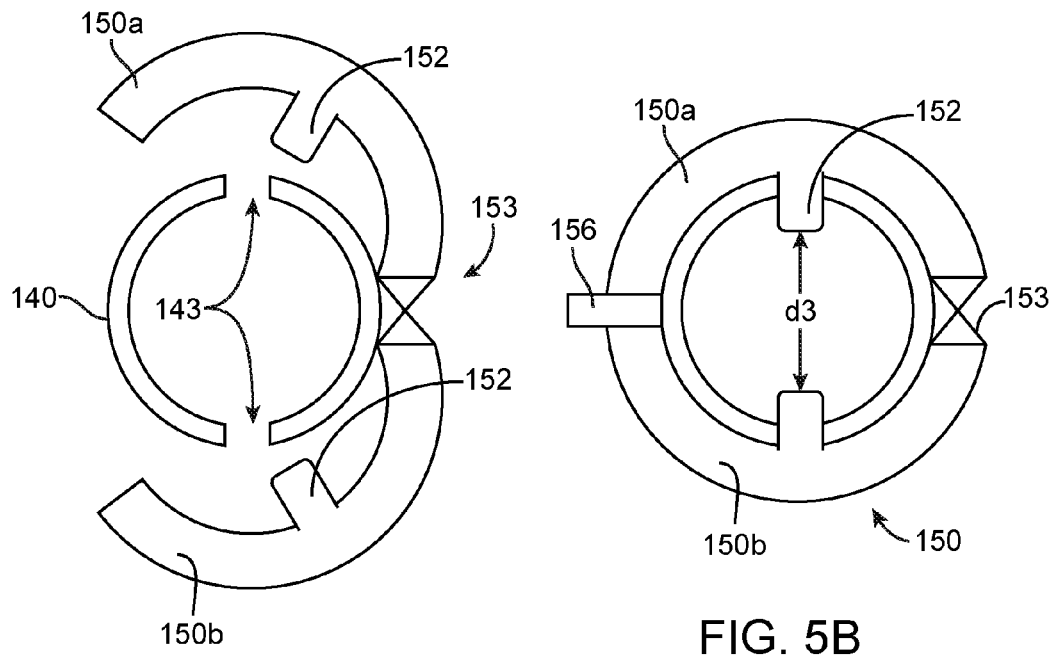
FIG. 5A
FIG. 5B
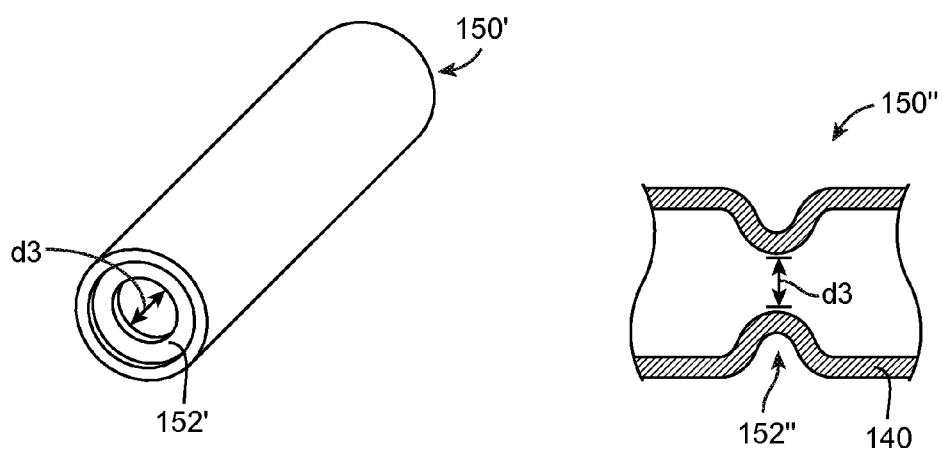
FIG. 5C
FIG. 5D

PROTECTIVE SHEATH ASSEMBLY FOR A POLYMER SCAFFOLD

FIELD OF THE INVENTION

The present invention relates to drug-eluting medical devices; more particularly, the invention relates to protective sheaths for scaffolds and stents crimped to a delivery balloon.

BACKGROUND OF THE INVENTION

A variety of non-surgical interventional procedures have been developed over the years for opening stenosed or occluded blood vessels in a patient caused by the build up of plaque or other substances in the walls of the blood vessel. Such procedures usually involve the percutaneous introduction of an interventional device into the lumen of the artery. In one procedure the stenosis can be treated by placing an expandable interventional device such as an expandable stent into the stenosed region to expand and hold open the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands to a deployed or expanded state within a vessel when a radial restraint is removed, while the former relies on an externally-applied force to configure it from a crimped or stowed state to the deployed or expanded state.

Self-expanding stents formed from, for example, shape memory metals or super-elastic alloys such as nickel-titanum (NiTi) which are designed to automatically expand from a compressed state when the radial restraint is withdrawn or removed at the distal end of a delivery catheter into the body lumen, i.e. when the radial restraint is withdrawn or removed. Typically, these stents are delivered within a radially restraining polymer sheath. The sheath maintains the low profile needed to navigate the stent towards the target site. Once at the target site, the sheath is then removed or withdrawn in a controlled manner to facilitate deployment or placement at the desired site. Examples of self-expanding stents constrained within a sheath when delivered to a target site within a body are found in U.S. Pat. No. 6,254,609, US 20030004561 and US 20020052640.

Balloon expanded stents, as the name implies, are expanded upon application of an external force through inflation of a balloon, upon which the stent is crimped. The expanding balloon applies a radial outward force on the luminal surfaces of the stent. During the expansion from a crimped or stowed, to deployed or expanded state the stent undergoes a plastic or irreversible deformation in the sense that the stent will essentially maintain its deformed, deployed state after balloon pressure is withdrawn.

Balloon expanded stents may also be stored within a sheath, either during a transluminal delivery to a target site or during the assembly or in the packaging of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating through interaction similar to forces at play when the blades and/or stent struts are misaligned during the diameter reduction. Examples of stents that utilize a sheath to protect the stent during a crimping process are found in U.S. Pat. Nos. 6,783,542 and 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. The polymer scaffold described in US 2010/0004735, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it is believed that biodegradable scaffolds, as opposed to a metal stent, allow for improved healing of the anatomical lumen and reduced incidence of late stent thrombosis. For these reasons, there is a desire to treat a vessel using a polymer scaffold, in particular a bioresorbable polymer scaffold, as opposed to a metal stent, so that the prosthesis's presence in the vessel is for a limited duration. However, there are numerous challenges to overcome when developing a delivery system having a polymer scaffold.

Polymeric materials considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. Suitable polymers have a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly a bioresorbable polymer such as PLLA or PLGA. Challenges faced when securing a polymer scaffold to a delivery balloon are discussed in U.S. patent application Ser. No. 12/861,719.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal can mean less concern over the metal stent—balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site. Consequently, sheaths for metallic stents are often solely protective, preventing contamination or mechanical damage to the stent and coating. They do not need to be closely fitted to prevent stent recoil on aging and storage.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, the material generally is incapable of being worked to the degree that a metal stent may be worked without introducing deployed strength problems, such as excessive cracking in the material. Recoil of the crimped structure, therefore, is a problem that needs to be addressed.

In view of the foregoing, there is a need to address the challenges associated with securing a polymer scaffold to a delivery balloon and maintaining the integrity of a scaffold-balloon catheter delivery system up until the time when the scaffold and balloon are delivered to a target site within a body. Related to these objectives, there is a need to improve the design and handling of a sheath assembly that is removable (prior to implantation) without causing damage or dislodgment of the crimped scaffold underneath. There is also a need to improve upon sheaths for, or removal of sheaths from stents.

SUMMARY OF THE INVENTION

The invention is directed to sheaths and/or sheath assemblies used to maintain a polymer scaffold balloon engagement and delivery system profile as well as methods for assembly of a medical device including a balloon expandable polymer scaffold contained within a sheath. The invention is also directed to a sheath and methods for applying a sheath and sheath assembly that enables the sheath to be easily removed by a medical professional, e.g., a doctor, so as to minimize disruption to a crimped scaffold-balloon engagement or damage to the crimped scaffold. Sheaths and sheath assemblies according to the invention are removed before the medical device is introduced into a mammalian body. The invention is further directed to sheaths and their use with stents.

Sheaths according to the invention are particularly useful for maintaining scaffold-balloon engagement and desired delivery profile following a crimping process where the scaffold is crimped down to achieve a smaller crossing-profile, or crimped diameter. A scaffold formed at a larger diameter, near to or greater than the intended deployed diameter, can exhibit enhanced radial strength when supporting a vessel, as compared to a scaffold formed nearer to a crimped diameter. A scaffold formed near to a deployed diameter, however, increases the propensity for elastic recoil in the scaffold following the crimping process, due to the shape memory in the material. The shape memory relied on for enhancing radial strength at deployment, therefore, also introduces greater elastic recoil tendencies for the crimped scaffold. Recoil both increases the crossing profile and reduces the scaffold-balloon engagement needed to hold the scaffold on the balloon. In one aspect, the invention is directed to maintaining the crossing profile and/or maintaining balloon-scaffold engagement for scaffolds formed near to a deployed diameter.

In another aspect, the invention is directed to a method of assembly of a catheter that includes crimping a polymer scaffold to a balloon of the catheter and within a short period of removal of the scaffold from the crimper placing a restraining sheath over the scaffold. The steps may further include applying an extended dwell time following a final crimping of the scaffold, followed by applying the restraining sheath. Both the crimping dwell time and applied restraining sheath are intended to reduce recoil in the crimped scaffold. The restraining sheath may include both a protecting sheath and a constraining sheath.

In another aspect, the invention is directed to a sterilized medical device, e.g., by E-beam radiation, contained within a sterile package, the package containing a scaffold crimped to a balloon catheter and a sheath disposed over the crimped scaffold to minimize recoil of the crimped scaffold. The sheath covers the crimped scaffold and may extend beyond the distal end of the catheter to facilitate removal from the scaffold. The sheath may extend at least the length of the scaffold beyond the distal end of the catheter. At the distal end of the sheath there is a portion configured for being manually grabbed and pulled distally of the catheter to remove the sheath from the catheter.

In another aspect, a medical device is contained within a protecting tube or coil that has a member forming a reduced clearance within the tube lumen. The reduced clearance interferes with a sheath disposed over the scaffold when the tube is pushed away from a proximal catheter end or the catheter drawn out from a proximal end of the tube. In a preferred embodiment the sheath is a two-piece sheath including a constraining sheath and protecting sheath portion.

In another aspect, the invention is directed to an apparatus and methods for removing a sheath pair from a scaffold in a safe, intuitive manner by a health professional. According to this aspect of the invention, the sheath pair may be removed by a medical specialist such as a doctor without risk of the scaffold becoming dislodged from the balloon or damaged, such as when the sheath pair is accidentally removed in an improper manner by a health professional.

Sheaths arranged according to the invention provide an effective radial constraint for preventing recoil in a crimped scaffold, yet are comparatively easy to manually remove from the scaffold. A sheath that applies a radial constraint can be difficult to remove manually without damaging the crimped scaffold, dislodging or shifting it on the balloon. In these cases it is desirable to arrange the sheaths in a manner to apply an effective radial constraint yet make the sheaths capable of manual removal in a safe and intuitive manner. By making the sheath removal process easy to follow and intuitive, the possibility that a health professional will damage the medical device when removing the sheath is reduced.

In accordance with the foregoing, there is a scaffold, medical device, method for making such a scaffold, or method for assembly of a medical device (such as a scaffold-balloon catheter assembly) comprising such a scaffold having one or more, or any combination of the following things (1)-(37):

(1) A one or two piece sheath assembly disposed over a scaffold. A sheath or sheath portion applies a radial constraint to reduce recoil of the scaffold. A one-piece sheath applying a radial constraint is described in FIGS. 5 and 6A-6D of US2012/0324696.

(2) Ratio of crimped diameter to balloon nominal inflation diameter or expanded diameter is greater than about 2, 2.5 or greater than about 3 or 4; and/or the ratio of pre-crimp diameter to balloon nominal diameter is about 0.9 to 1.5.

(3) The catheter and scaffold are configured as a medical device suitable for being implanted within a body only after both a sheath disposed over the scaffold and a tube are removed. The catheter is not configured for being introduced into the patient until the sheath pair and/or tube are removed.

(4) A scaffold crimped to a balloon and a sheath disposed over the scaffold. The scaffold is configured for being introduced into a mammalian body only after the sheath is removed from the scaffold. And means for removing the sheath from the scaffold. The scaffold may be at least partially contained within a tube when the sheath is being removed. The means may include a member on the tube and/or a sheath configured for being partially or fully removed before a protecting sheath is removed.

(5) A catheter including a sheath over a scaffold. The catheter is within a tube. And a means for removing the sheath from the scaffold while the scaffold is at least partially within the tube.

(6) A method of maintaining a low crossing profile or retention between a scaffold and balloon, comprising: crimping; dwelling to reduce recoil; placing a first sheath over the scaffold; removing the first sheath; placing a second sheath; wherein prior to implantation second sheath is removed (7) A tube having a member that interferes with a sheath when the sheath is removed from the tube.

(8) The protecting sheath is a one or two piece sheath.

(9) The tube has a proximal and distal section; the distal section can be removed from the proximal section to facilitate crimping or inspection while the catheter remains within the proximal section.

(10) A protecting sheath, when protecting a crimped scaffold, covers at least the entire length of the scaffold and balloon, and may extend beyond a distal tip of the catheter by at least a scaffold length.

(11) The protecting sheath has one or two flared, stepped or notched ends, or no stepped or notched ends.

(12) A constraining sheath length that is less, equal to, or greater than the protecting sheath length.

(13) A method for making a sheath includes placing a protecting sheath within a constraining sheath, and then raising the ends of the protecting sheath when the protecting sheath is within the constraining sheath, where the raised ends resist removal of the constraining sheath from the protecting sheath. The method may further include attaching a tube to the constraining sheath to from a two-piece constraining sheath. The constraining sheath may be longer, the same length or shorter than the protecting sheath.

(14) The sheath may comprise PTFE, PVDF, fluoropolymer, polyethylene, polypropylene, nylon, nylon copolymers, Pebax, polyacetal, or polyimide.

(15) The polymer comprising the scaffold is bioresorbable, or the stent comprises a durable, non-bioresorbable, or non-bioerodible polymer.

(16) A constraining sheath has at least a first and second portion distinguished by their outer diameters—a first outer diameter corresponding to the first sheath portion that can apply a radial constraining force on the scaffold, and a second outer diameter, greater than the first outer diameter, corresponding to the second sheath portion that is located distal and/or proximal of the first sheath portion when the first sheath portion is disposed over the scaffold.

(17) A catheter having a sheath wherein the sheath has a diameter greater than any other part of the catheter, wherein the catheter when removed from a tube causes the sheath to be removed while at least part of the catheter remains inside the tube.

(18) A tube includes a member that interferes with a sheath constraining a scaffold when a catheter supporting the scaffold is being removed from the tube.

(19) The member can be releasably attached to the tube, or attached to the tube before or after the catheter is inserted into the tube.

(20) Any of the embodiments of structure forming the member and/or tube 140 having a portion defining the diameter d3 for interfering with constraining sheath described in connection with FIGS. 5A-5D and 6A-6B.

(21) A member is fitted to, formed in, or attached to a tube after crimping and sheath placement; and/or the tube has a separable distal end for access to the balloon during crimping a sheath placement.

(22) A one or two piece tube and catheter with the tube. For the one-piece tube a member is disposed on the tube after the catheter (with sheath over scaffold) is within the tube. For the two piece tube the member may be pre-disposed on the tube before the catheter including a sheath disposed over a scaffold is placed within the tube.

(23) The member may be disposed at either the proximal or distal end of the tube.

(24) The member interferes with only a sheath disposed over the scaffold. No other portions of the scaffold, catheter or balloon are interfered with by the member. They may be freely removed from the tube without obstruction.

(25) An apparatus including a sheath disposed over a crimped scaffold, the sheath and catheter being disposed within a rigid tube, the tube's bore defining a clearance that is substantially less than a diameter of the sheath.

(26) The scaffold may be crimped to a balloon catheter, the catheter may be contained within a tube and the catheter (with or without the tube) may be contained within an E-beam sterilized package.

(27) Crimping of the scaffold to the balloon includes placing a one-piece sheath over the scaffold and/or a two-piece sheath after crimping to reduce recoil.

(28) A method of maintaining a low crossing profile or retention between a scaffold and balloon, comprising: crimping; dwelling to reduce recoil; placing a first sheath over the scaffold; removing the first sheath;

placing a second sheath; wherein prior to implantation the second sheath is removed.

(29) A method of assembly including placing a catheter within a first tube wherein only the distal end of the catheter is outside the tube, crimping; and attaching a second tube to the first tube to cover the distal end. The tube may include a clearance at either distal or proximal end.

(30) A one or two piece sheath in combination with a stent or scaffold.

(31) A method for maintaining a low crossing profile and/or retention for a polymer includes crimping a scaffold to a balloon, placing a first sheath over the crimped scaffold; and replacing the first sheath with a second sheath; wherein the crimped scaffold is adapted for being passed through a mammalian body only after the second sheath is removed. Before or after replacing the first sheath the scaffold may be placed in a tube adapted to remove the second sheath.

(32) An apparatus including a catheter, the catheter including a scaffold comprising a polymer (or a stent comprising a durable polymer or a metal or metal alloy), the scaffold being crimped to a balloon; a sheath disposed over the scaffold; a tube containing at least a portion of the catheter; and a member disposed within the tube, wherein the member partially or fully removes the sheath from the scaffold when the tube is separated from the catheter; and wherein the catheter is configured for being introduced into a mammalian body only after the sheath is removed from the scaffold.

(33) The apparatus of (32) or (34) or method of (36), in combination with one of, more than one of, or any combination in any order of the following list of things: wherein the scaffold is formed from a radially expanded tube having a pre-crimp diameter that is at least about 1.5, 2, 3, or 4 times the crimped diameter of the scaffold; wherein the member is disposed at an end of the catheter or the tube; wherein the tube is rigid compared to the sheath; wherein the tube extends substantially the entire length of a shaft of the catheter; wherein the sheath includes a constraining portion and a protecting portion, the constraining portion applying a radial inward force on the crimped scaffold to limit recoil of the scaffold; wherein the sheath is a two piece sheath; wherein the sheath includes a second member that exceeds the clearance, so that the sheath is partially or fully pulled or pushed off the scaffold when the second member encounters the clearance; and/or wherein the member is a clip, rim, flange or portion of the tube.

(34) An apparatus for delivery of a medical device, including a balloon catheter including a balloon having a nominal inflation diameter; a scaffold formed form a radially expanded tube comprising a polymer; the scaffold being crimped to the balloon and having a crimped diameter, wherein the balloon nominal inflation diameter is about 2, 3 or 4 times greater than the crimped diameter of the scaffold; a constraining sheath disposed over the scaffold, the sheath being configured for minimizing recoil of the scaffold so as to maintain the crimped diameter; and a rigid tube containing the catheter; wherein the catheter is adapted for being passed through a mammalian body only after the catheter is removed from the tube.

(35) The apparatus of (32) or (34) or method of (36), in combination with one of, more than one of, or any combination in any order of the following list of things: wherein the scaffold has a morphology characterized by (1) substantially radially aligned polymer chains resulting from a biaxial expansion of the scaffold in the radial direction by between about 200 to 400% of a pre-expansion tube diameter, and (2) the scaffold is crimped from the tube or pre-crimp diameter to the crimped diameter that is at least 2-3 times reduced from the tube diameter; wherein the scaffold is made from a polymer composition comprising PLLA; wherein the polymer chains of the crimped scaffold are aligned substantially in a radial direction resulting from a radial expansion of between about 400% and 450% and axial expansion of between 150% and 200%, or 10% and 50%; wherein the tube is configured to partially or fully remove the sheath from the scaffold, or partially or fully remove a sheath constraining portion from the catheter when the catheter is withdrawn from a proximal end the tube; and/or wherein the catheter comprises a shaft and a hub and wherein the entire shaft is contained within the tube.

(36) A method, including the steps of providing a tube having a lumen, and contained within the lumen a catheter including a scaffold crimped to a balloon, wherein a sheath constrains the scaffold; and removing the sheath from the catheter by removing the catheter from the tube.

(37) The apparatus of (32) or (34) or method of (36), in combination with one of, more than one of, or any combination in any order of the following list of things: wherein the tube extends from at least a catheter distal end to a catheter proximal end; wherein the scaffold and catheter are configured for implantation within a body only after both the sheath and tube are removed; wherein the tube is rigid compared to the sheath; and/or wherein the removing the sheath step includes engaging a first member of the tube with a second member of the catheter.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 5A-5B shows a clip before and after being attached to the tube of FIG. 1.

FIG. 5C shows a sleeve having a flange. The sleeve is attached to an end of a tube.

FIG. 5D shows a rim formed in a tube.

DETAILED DESCRIPTION OF EMBODIMENTS

Figure 1:
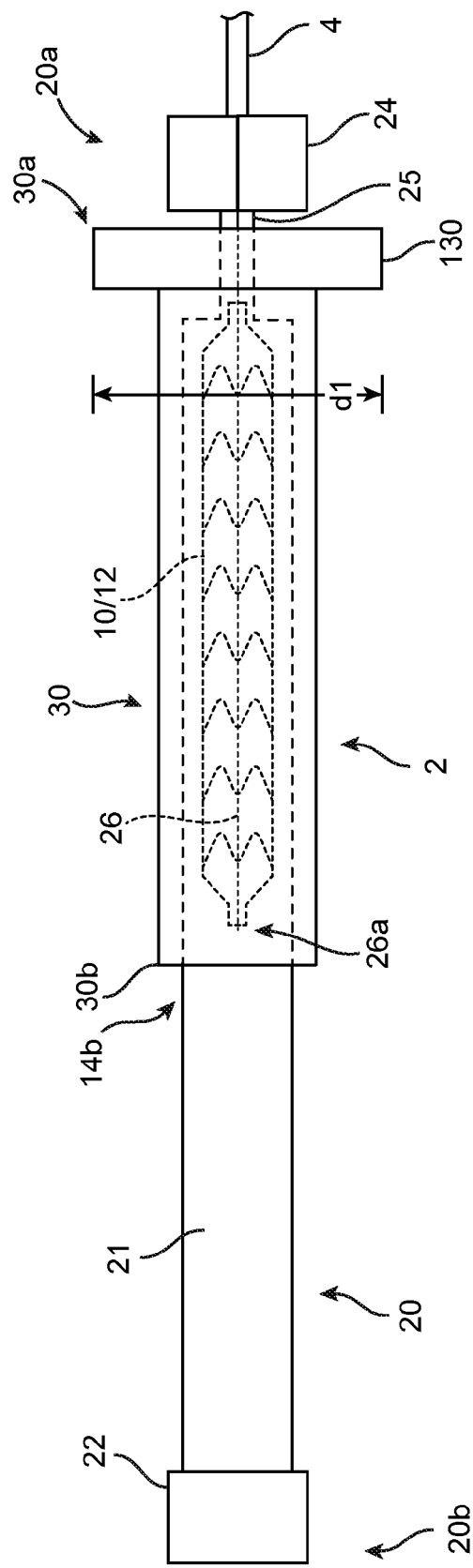
FIG. 1 is a side view of a polymer scaffold-balloon catheter assembly with a first pair of sheaths placed over the crimped scaffold. The sheaths may be removed when the catheter assembly is withdrawn from a protecting tube.

For purposes of this disclosure, the following terms and definitions apply:

The term "about" means 20%, 10%, 5%, 2% or 1% less or more than a stated value, a range or each endpoint of a stated range, or a one-sigma variation from a stated mean value. The term "substantially" refers to at least a 30%, 20%, 10%, 5%, 2% or 1% deviation from a value or range. For example, d1 substantially less than d2 means d1 is at least 30%, 20%, 10%, 5%, 2% or 1% less than d2.

The term "rigid" is a relative term used to describe something that is substantially stiffer than some other thing. For example, a first sheath or tube that is radially rigid, rigid in the radial direction, or simply rigid as compared to a second sheath or tube means that the first sheath/tube is incompressible compared to the second sheath, or essentially does not deform when an external, radially compressive force or pinching force is applied as compared to the second sheath, for the same applied load.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an OD of a tube, or the scaffold before it is crimped to a balloon. Similarly, a "final crimped diameter" means the OD of the scaffold when crimped to a balloon and removed from a crimping mechanism just prior to sheath placement. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter. A "partial crimp" diameter is a diameter attained after a scaffold or segment is crimped to a diameter less than a pre-crimp diameter and greater than the final crimp diameter. A partial crimp diameter can be an intermediate diameter after crimping from a pre-crimp diameter to about the nominal or over inflated diameter of the balloon to which the scaffold will be crimped. An example of a partial crimping diameter is described by the scaffold diameter following "Stage II" in FIGS. 3A and 4A, and described in U.S. application Ser. No. 13/644,347 . A crimping mechanism or crimper may correspond to a linkage/mechanism including cooperating blades or teeth configured to apply an approximately uniform radial pressure on a scaffold to reduce its diameter to a final crimp diameter. The crimping performed by the crimping mechanism may include a polymer material disposed between the teeth and surface of a scaffold; as example of such arrangement being found in US 2012/0042501.

"Recoil" means the response of a material following the plastic/inelastic deformation of the material and in the absence of externally applied forces, e.g., vessel contraction. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

"Axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. Thus, a link spaced 180 degrees from another link means 180 degrees as measured about the circumference of the tubular construct.

"Radial" refers to a direction, orientation, or line that is perpendicular or substantially perpendicular to the central axis of the stent or the central axis of a tubular construct and is sometimes used to describe a circumferential property, i.e. radial strength.

A polymer scaffold according to a preferred embodiment is formed from a radially expanded or biaxially expanded extruded PLLA tube. The degree of radial expansion (RE) and axial expansion (AE) that the polymer tube undergoes can characterize the degree of induced circumferential molecular and crystal orientation as well as strength in a circumferential direction. In some embodiments the RE is about 400% and the AE is 40-50%. Other embodiments of processing parameters, RE and AE expansions considered within the scope of the disclosure are found in U.S. application Ser. No. 13/840,257 filed Mar. 15, 2013.

The scaffold is laser cut from the expanded tube. The diameter of the tube is preferably selected to be about the same, or larger than the intended deployed diameter for the scaffold to provided desirable radial strength characteristics, as explained earlier. The scaffold is then crimped onto the balloon of the balloon catheter. Preferably, an iris-type crimping mechanism is used to crimp the scaffold to the balloon. The desired crimped profile for the scaffold is ½ or less than ½ of the starting (pre crimp) diameter of the expanded tube and scaffold. In the embodiments, the ratio of the starting diameter or pre-crimp diameter to the final crimp diameter may be 2:1, 2.5:1, 3:1, or higher and the pre-crimp diameter may be about 0.9 to about 1.5 higher than the balloon nominal inflation diameter. The ratio of pre-crimp or intermediate crimp diameter to final crimped diameter may be greater than a ratio of expanded or post-dilation diameter to the final crimped diameter of the scaffold.

The pre-crimp memory in the scaffold material following crimping will induce some recoil when the scaffold is removed from the crimper. While a dwell period within the crimper can reduce this recoil tendency, there is residual recoil to restrain while the scaffold awaits use. This is done by placing a restraining sheath over the scaffold after the crimper blades are released and the scaffold removed from the crimper head. This need to reduce recoil is particularly evident when the diameter reduction during crimping is high, e.g., as in above examples, since for a larger starting diameter compared to the crimped diameter the crimped material can have higher recoil tendencies. Examples of polymers that may be used to construct sheaths described herein are Pebax, PTFE, polyethylene, polycarbonate, polyimide and nylon. Examples of restraining sheaths for polymer scaffold, and methods for attaching and removing restraining sheaths for polymer scaffold are described in US20120109281, US20120324696 and U.S. Pat. No. 8,414, 528, and U.S. application Ser. No. 13/708,638.

FIG. 1 shows a side view of a distal portion of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is slid over the outer surface of the protecting sheath 20 to position it over the scaffold 10. Before inserting the catheter assembly 2 distal end within a patient, both the constraining sheath 30 and protecting sheath 20 are removed by a health professional.

The sheaths 20, 30 provide an effective radial constraint for reducing recoil in the crimped scaffold 10. Yet the sheaths 20, 30 are also easily removed by a health professional at the time of a medical procedure by pulling or pushing the outer sheath 30 towards the distal end of the scaffold 10 and balloon 12 using a tube, within which is the catheter assembly 2. This aspect of the disclosure (involving a tube) is described in more detail later. The removal technique for sheaths 20, 30 includes a similar motion to the removal technique required for other coronary device products, where a single, non-constraining sheath is used to cover and protect the stent. In those cases the sheath is grasped by the doctor or technician's gloved hands and pulled off towards the distal end of the device. But, as described herein, a sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

The constraint imposed by the sheaths 20, 30 maintain the scaffold 10 at essentially the same, or close to the same diameter it had when removed from the crimping mechanism. The sheath 30 is tightly fit over the sheath 20 and scaffold 10 so that the radial inward force applied on the scaffold 10 can prevent or reduce recoil in the scaffold 10. The health professional may then remove both sheaths at the time of the medical procedure. As such, any potential recoil in the scaffold 10 prior to using the medical device is minimized.

The sheath 30, although imposing a tight fit on the scaffold 10 (through sheath 20), can be easily removed by a health professional without risk of the scaffold 10 being accidentally pulled off of the balloon 12. This may be done in a number of ways according to the disclosure; at least one of the ways based on the manner in which the sheath 20 is positioned and removed from the scaffold 10. If there are excessive pulling forces on the scaffold 10 when sheaths are removed, the catheter shaft 4 may be damaged, the scaffold 10 may dislodge from a balloon 12, or shift on the balloon 12; thereby reducing scaffold-balloon engagement relied on to hold the scaffold 10 to the balloon 12.

When the scaffold 10 is constrained by sheath 30, as in FIG. 1, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and the smaller the pre-stressed inner diameter size for the sheath 30 the higher this constraint will be on the scaffold 10. However, the sheath 30 thickness should not be too thick, nor its inner diameter too small as this will make it difficult to slide the sheath 30 over, or remove the sheath 30 from the scaffold 10. If excessive force is needed to reposition the sheath 30, the scaffold 10 can dislodge from the balloon 12 or the scaffold 10 and catheter shaft 4 can become damaged when the sheath 30 is moved.

If only sheath 30 were applied, i.e., the sheath 20 is not present, the amount of preload that the sheath 30 could apply to the scaffold 10 without affecting scaffold-balloon engagement would be limited. However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The protecting sheath 20 therefore serves to protect the integrity of the scaffold-balloon structure as the sheath 30 is repositioned relative to the scaffold 10. An example of a one-piece sheath that is capable of performing in a similar manner is found in US2012/0324696 at FIGS. 5 and 6A-6D.

Figure 3A:
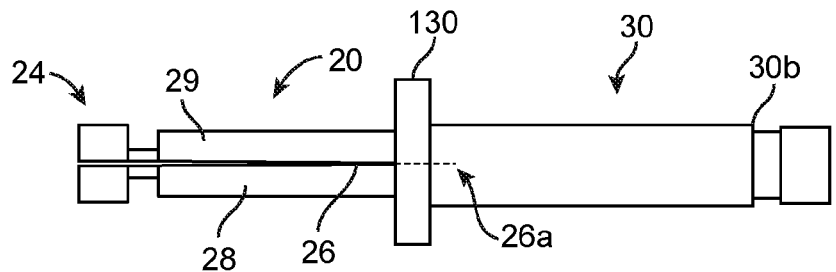
FIGS. 3A-3D illustrate a method of securing the sheath pair of FIG. 2A to a distal end of the catheter assembly of FIG. 1.
Figure 3B:
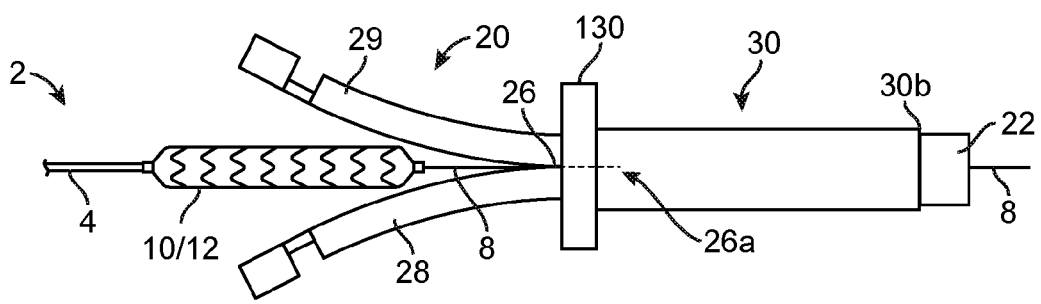

The protecting sheath 20 extends over the entire length of the scaffold (as shown) and beyond the distal tip of the catheter assembly 2 (as can be seen in FIG. 3B) may the sheath 20 extend. The protecting sheath 20 is preferably formed from a unitary piece of polymer material, which is shaped to form differently sized portions 22, 24 and for protecting the scaffold/balloon 10/12.

At the distal end 20b of sheath 20 there is a raised end 22 in the form of a cylinder section having a larger diameter than the body portion 21 of the sheath 20 to the right of end 22 which covers the scaffold 10 in FIG. 1. Raised end 22 provides an abutting surface with respect to distal movement of sheath 30, i.e., end 30b of sheath abuts end 22 when sheath 30 is moved to the left in FIG. 1. End 22 may alternatively take the shape of a cone with the largest diameter end of the cone being the most distal end of the sheath 20. The raised end 22 may function to remove the sheaths 20, 30, as explained below.

Figure 2A:
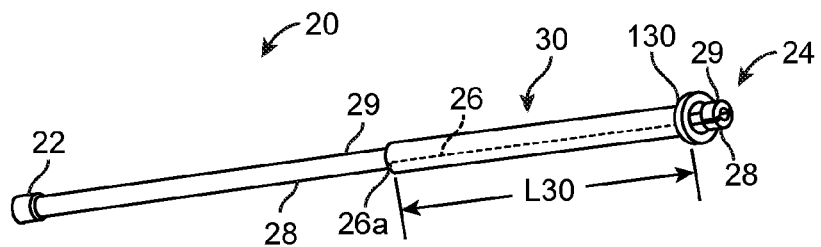
FIG. 2A is a perspective view of the sheath pair of FIG. 1.

The protecting sheath 20 has a cut 26, extending from the proximal end 20a to a location about at the distal the tip of the catheter assembly 2 (or sheath 20). The cut 26 forms an upper and lower separable halve 28, 29 of the sheath 20 (FIG. 2D). These halves 29, 28 are configured to freely move apart when the sheath 30 is positioned towards the distal end 20b. The location 26a may be thought of as a living hinge 26a about which the upper half 29 and lower half 28 of the sheath 20 can rotate, or deflect away from the scaffold 10. When sheath 30 is moved distally of the scaffold 10 in FIG. 1, the halves 28, 29 will tend to open up naturally, due to the preload applied by sheath 30 near hinge 26a (the separable halves 28, 29 can be more clearly seen in FIGS. 2A-2D). This arrangement for halves 29, 28 provides easy removal of sheath 20 from the scaffold 10, with minimal disruption to scaffold-balloon structural integrity, after sheath 30 is moved towards distal end 20b. When sheath 30 is being fitted over the scaffold 10 or removed from the scaffold 10, the presence of the halves 28, 29 prevent direct contact between the sliding sheath 30 and the surface of the scaffold 10.

Sheath 20 may alternatively be formed as two completely separable halves, e.g., as halves 145a and 140a illustrated in FIG. 11C of US2012/0324696 or as the same two halves shown in FIG. 2 but with the cut 26 running the length of, or substantially the entire length of the sheath 20. In the case of the former sheath 20 embodiment, sheath 150 of FIG. 11C of US2012/0324696 is replaced by the sheath 30 illustrated in FIG. 1 or other suitable embodiments thereof, discussed more fully below.

Figure 1A:
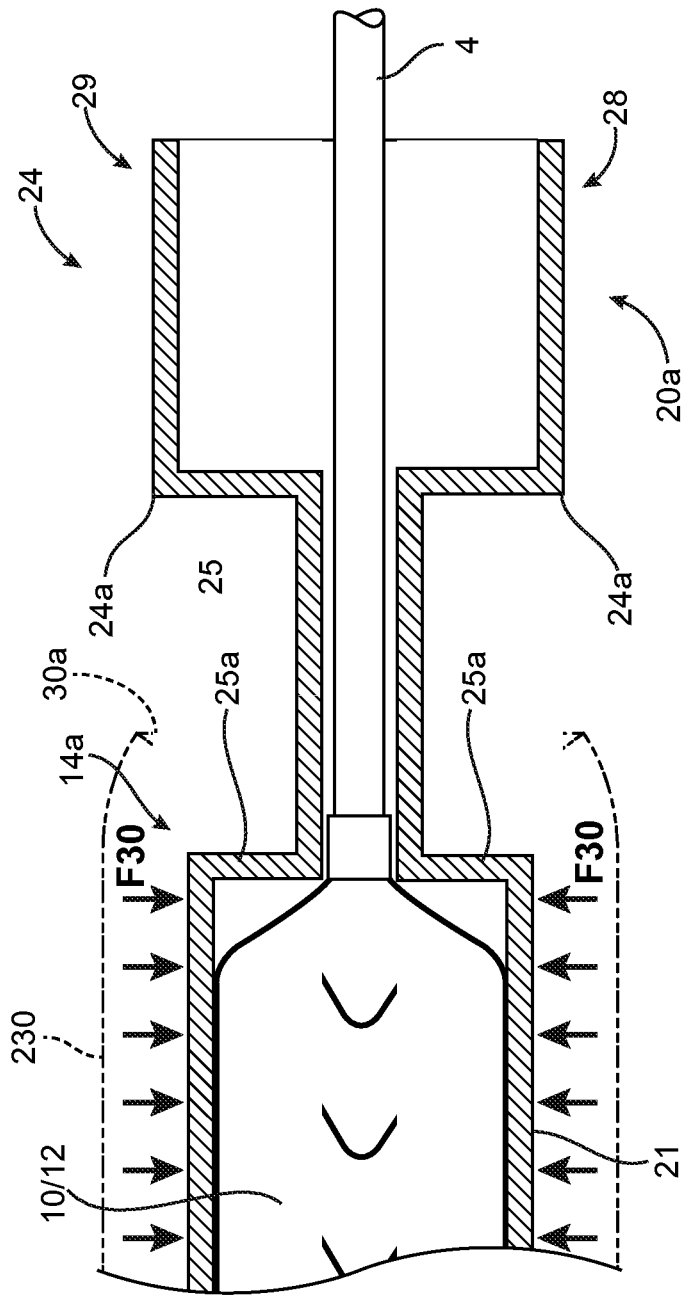
FIG. 1A shows a side view cross-section of a portion of the device of FIG. 1 at a proximal end thereof, but with a first constraining sheath replaced by a constraining sheath as shown in FIGS. 7A-7D.

FIG. 1A shows a proximal end 20a of sheath 20 with another embodiment of a constraining sheath—an outer sheath 230 (see FIGS. 7A-7C)—disposed over the sheath 20. Referring to FIG. 1A, at the proximal end 20a there are portions 24 and 25 formed when the combined proximal ends of halves 28, 29 are brought together as in FIG. 1. When the halves 28, 29 are brought together notch portion 25 and raised (or stepped) portion 24, similar to end 22, are formed. The notched portion 25 has an outer diameter less than the inner diameter of the portion 21 of the sheath 30/230 that covers the scaffold 10, as well as the outer diameter of the scaffold/balloon 10/12. The raised portion 24 has a diameter greater than the body portion 21, which refers to the inner diameter of the sheath 30 or sheath 230 in FIG. 1A and the diameter for end 24 may be the same as the diameter for end 22. The raised portion 24 provides an abutment or stop 24a preventing a proximal end 30a of the sheath 30/230 from moving to the right in FIG. 1. The portion 24 may prevent the sheath 30/230 from sliding off of the scaffold 10 and/or locate the portion of end 30a of sheath 30/230 relative to sheath 20 proximal end 20a so that sheath 30/230 applies a uniform compressive force over the entire length of the scaffold. A compressive portion of the sheath 30/230 (discussed below) has a length about equal to the length of the portion 25 plus the scaffold/balloon length so that when end 30a abuts end 24 the sheath 30 will properly cover the entire scaffold/balloon 10/12 length.

Portion 25 discourages removal of the sheath 20 prior to removal of sheath 30 from the scaffold 10. Referring again to FIG. 1A, there is a close-up of the proximal end 20a with the sheath 230 (shown in phantom) replaced by the inwardly directed preload F30 it applies to sheath portion 21 when positioned over the scaffold 10. A distal end of portion 25 forms a ledge 25a. When sheath 30 is positioned over the scaffold 10 the inwardly directed preload F30 applied to sheath portion 21 urges the halves 29, 28 together. With the halves 28, 29 urged together, the scaffold/balloon proximal end 14a blocks movement of the sheath 20 to the left in FIG. 1A by interfering with the movement of the ledge 25a to the left. Thus, if a user attempts to pull the sheath 20 off prior to removing the sheath 230/30 from the scaffold 10 area (which can damage the scaffold/balloon integrity or catheter shaft 4), there will be resistance to this movement due to the ledges 25a abutting the balloon proximal end 14a (the ledge 25a thus may be thought of as an interference or interfering ledge part of the sheath 20). This resistance should indicate to the user that the sheaths 20, 30/230 are being removed in an improper manner. When the sheaths 20, 30/230 are removed properly, the first sheath 30 is moved to the distal end 20b of the sheath 20 (thereby removing the preload F30) so that the halves 28, 29 freely open up to allow the ledge 25a to easily pass over the scaffold 10 so that sheath 20 is removed without resistance. The user is thereby informed that the sheath 20 is removed properly when there is no resistance to removing the sheath 20 from the balloon-catheter assembly 2.

Thus, scaffold-balloon integrity is protected by the presence of the halves 28, 29 and the notched portion 25, as discussed above. The extended length of sheath 20, beyond the tip of the catheter assembly 2, e.g., is about equal to a length of the scaffold 10, the length of the sheath 30 or greater than both. This length beyond the distal tip facilitates an intuitive sliding removal or attachment of the sheath 30 from/to the scaffold 10 by respectively sliding the sheath 30 along the sheath 20 extension that is beyond the distal tip of the catheter assembly 2. The length of the sheath 20 that extends beyond the distal end of the catheter assembly 2 (length L21 in FIG. 4A of US2012/0324696) may depend on the choice of sheaths used. For example, from the perspective of the health professional removal process, if the sheath 20 is more stiff (e.g., higher wall thickness and/or modulus) relative to the sheath 30 then the length beyond distal end 4 for sheath 20 may be longer so that the halves 28, 29 of sheath 20 can be more safely displaced from the scaffold 10 by clearing the sheath 30 more distally of the scaffold 10. If the sheath 30 wall thickness and/or modulus is higher relative to sheath 20 than the length may be shorter since the sheath 30 will tend to naturally open up the halves 28, 29 as it is moved distally of the distal tip of the catheter assembly 2. Also, a thicker or higher modulus sheath 20 and/or sheath 30 may be desirable to increase the resistance to improper removal of sheath 20, e.g., as when a user attempts to remove sheath 20 with, or before removing sheath 30 from the scaffold 10 (as discussed earlier).

In a preferred embodiment the constraining sheath is made with a portion having a diameter greater than the diameter of other portions of the constraining sheath. When sheath 30 is positioned on a scaffold, as in FIG. 1, member 130 may define a diameter substantially greater than any other diameter along the length of the catheter portion received within a protecting tube or coil.

Figure 4A:
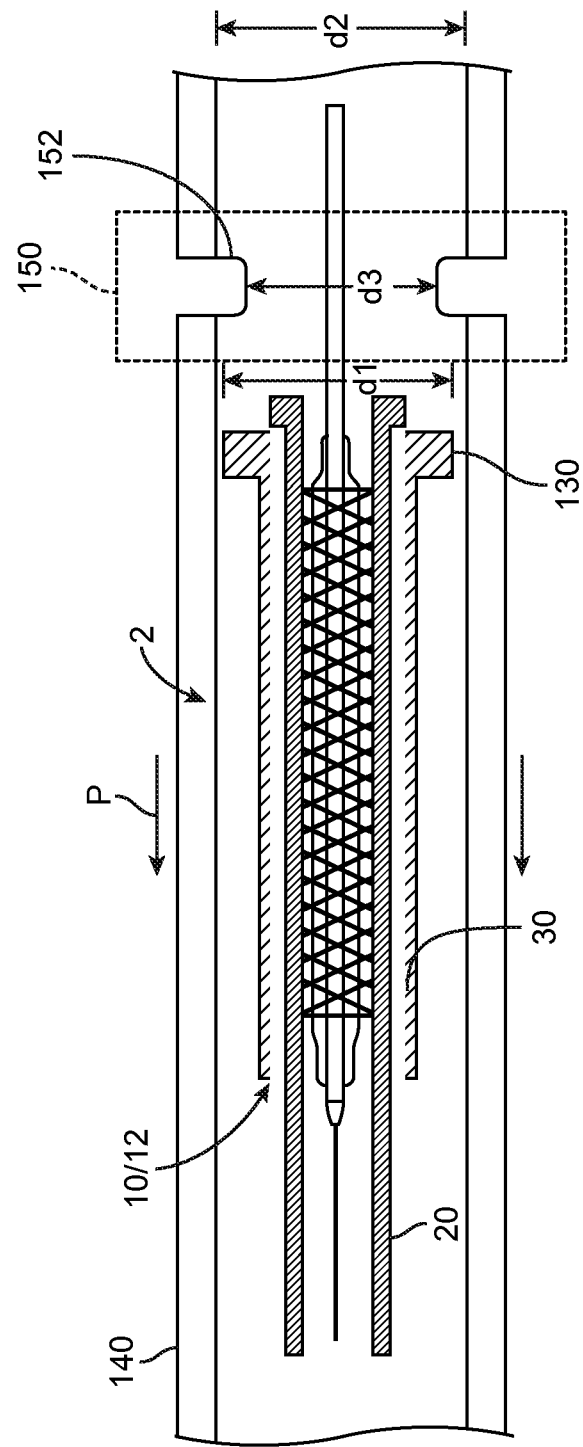
FIGS. 4A-4C illustrate a method of removing a sheath of FIG. 1 from the distal end of the catheter assembly of FIG. 1. The catheter assembly is within a tube.
Figure 4B:
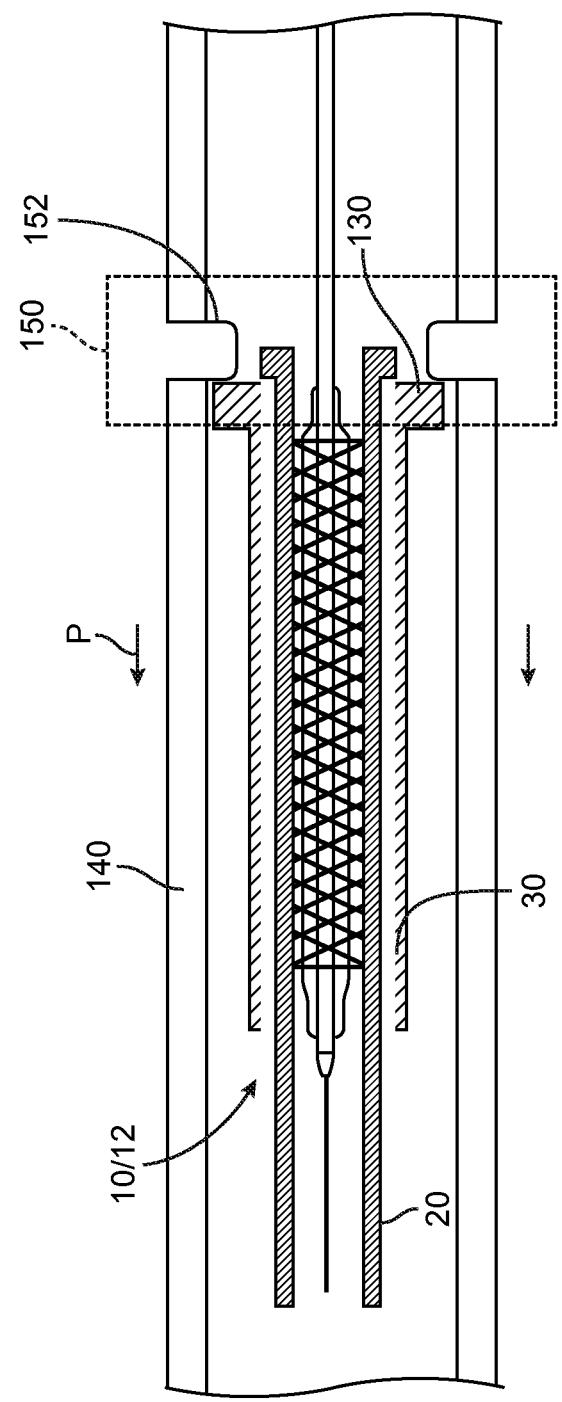
Figure 4C:
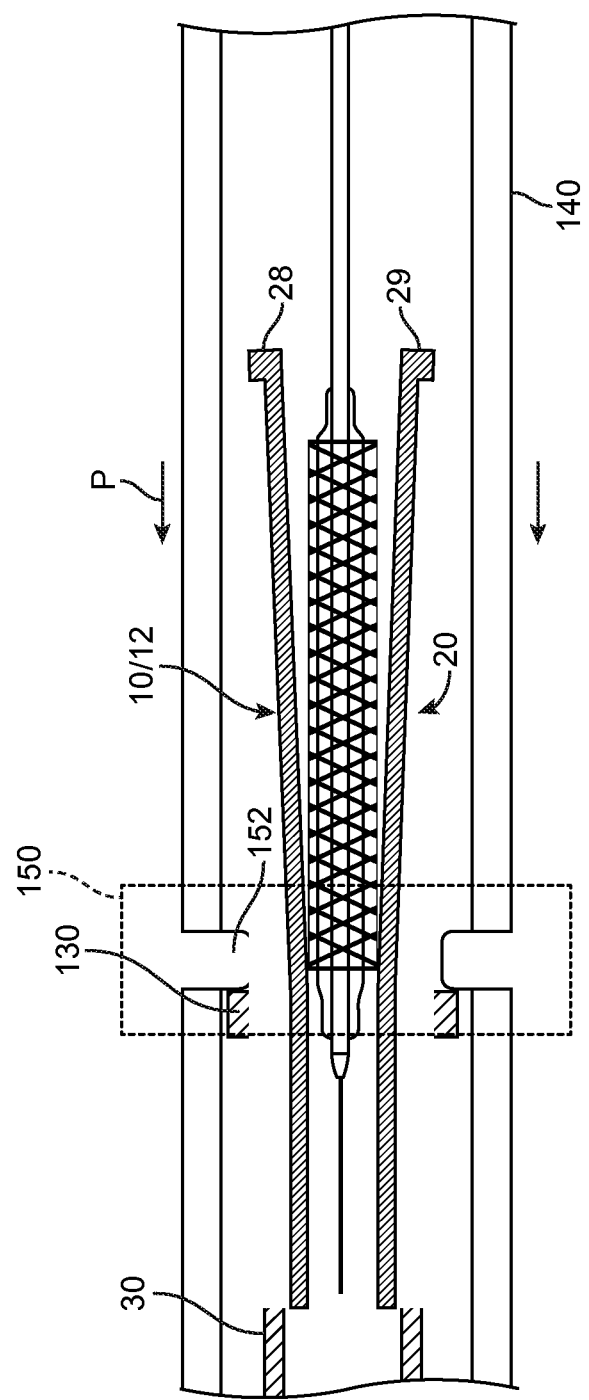

In one example, adjacent to, or at proximal end 30a of sheath 30 in FIG. 1 there is a raised portion 130 having a diameter d1. The diameter d1 is selected so that the sheath 30 is engaged by, or makes contact with a member disposed on a tube (or coil) when the catheter assembly 2 is being removed from the tube, as illustrated in FIGS. 4A-4C (discussed in more detail below). The portion 130 may be formed from the same material as sheath 30, e.g., start with a tube of diameter d1 and reduce or step-down to the diameter of the constraining portion of sheath 30 (FIG. 1) while leaving portion 130 at the original diameter d1. The portion 130 may be raised, flared out, or frusto-conical in shape, or a separate piece attached to the sheath 30 to form 130. The length of portion 130 may be such that when end 30a is abutting portion 24 the entire scaffold is receiving a uniform compressive force. In this regard, for a portion 130 formed by a flared out or raised in/out portion of the same tube used to form sheath 30, the portion 130 is proximal of the sheath 30 so that a uniform compressive force is applied over the entire length of the scaffold 10. In other embodiments—e.g., a welded annular piece forming the diameter d1, or 2, 3, 6, circumferentially-spaced tabs each forming an extent for sheath 30 equal to d1 when attached to the outer surface of sheath 30—the portion 130 may be located over the scaffold when sheath 30 is constraining the scaffold without affecting the radial compressive force anywhere over the scaffold length.

Figure 2B:
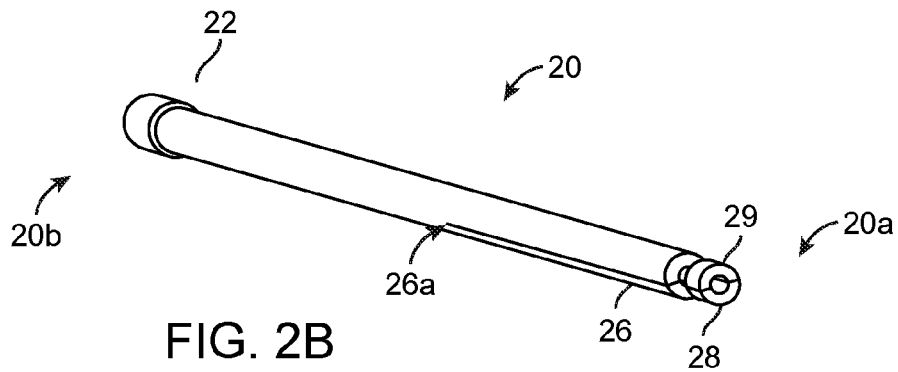
FIGS. 2B-2D show a side view, and first and perspective views of a protecting sheath of the sheath pair of FIG. 2A.
Figure 2C:
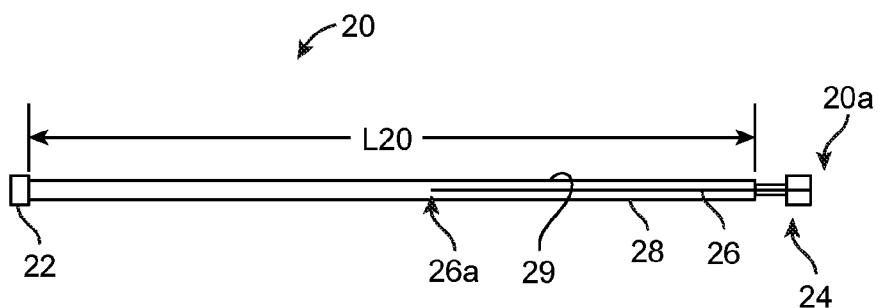
Figure 2D:
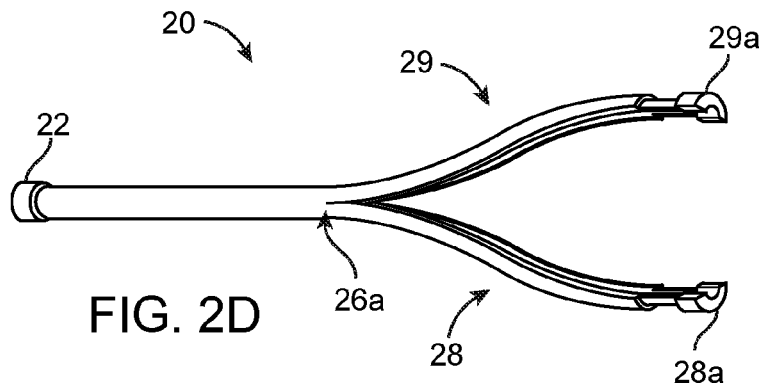

Referring to FIGS. 2B-2D, there are shown various views of the sheath 20. FIG. 2A shows the sheath 20 with the sheath 30. The constraining portion of sheath 30 referred to earlier, may have the length L30 such that sheath 30 applies a sufficiently uniform radial inward force or preload on the scaffold 10 when end 30a abuts end 24a (FIG. 1A). The length L30 is slightly greater than the length of the scaffold-balloon structure. The sheath 30 can be slid towards or away from the scaffold location (i.e., its location in FIG. 2A or FIG. 1) over the sheath outer surface 20. As noted earlier, the sheath 20 has separable upper and lower halves 29, 28 formed by a cut 26 made across the tube forming sheath 20. FIG. 2D is a perspective view of the upper and lower halves 28, 29 separated from each other. As can be appreciated from this view, the halves 28, 29 rotate about the hinge 26a when they separate. FIGS. 2B and 2C show an additional side and perspective view, respectively, of the sheath 20 showing the aforementioned structure, including the portions of notched or stepped portion 25 and end 24 (FIG. 1A) discussed earlier.

The length L20 in FIG. 2C may extend over the scaffold 10 length as well as a sufficient distance beyond the scaffold 10 so that the sheath 30 can be pushed onto the scaffold 10, and removed from the scaffold 10 while the halves 28, 29 are disposed over the scaffold 10. The length L20 may be at least twice the length of sheath 30, i.e., L20=2*L30, to achieve this purpose. This length should be sufficient to allow the upper and lower halves 28, 29 to peel or rotate about the living hinge 26a and freely away from the scaffold surface (as in FIG. 2D) without interference from the sheath 30 when sheath 30 abuts end 22.

As mentioned earlier, a thicker tube and smaller inner diameter for sheath 30 will cause the sheath 30 to apply a greater pre-load on the scaffold 10. The sheath 30 thickness and/or inner diameter size is selected with the sheath 20 in mind. That is, the sizing of one can determine what sizing to use for the other, based on achieving an appropriate balance among the amount of pre-load desired, the ease in which the sheath 30 can be placed over or removed from the scaffold 10 location, increasing resistance to improper removal of sheath 20 (ledge 25a abutting proximal end 14a, as discussed above) and avoiding disruption to the integrity of the scaffold-balloon structure, e.g., pulling the scaffold 10 off the balloon when the sheath 30 is being removed. For example, if a relatively thin and/or low modulus tube is used for sheath 20 (as compared to sheath 30), the sheath 30 will impose a higher localized pre-load on the scaffold 10. And the scaffold 10 is more likely to be affected by sheath 30 movement because the sheath 20 easily deforms under the movement of the sheath 30. If the sheath 20 is made thick and/or a higher modulus tube material is used for sheath 20 (compared to sheath 30) the scaffold 10 will not be as affected by movement of the sheath 30. And local changes in pre-load on the scaffold 10 will tend to be lower since the sheath 20 does not deform as easily under the movement of the sheath 30.

Referring to FIGS. 3A-3D, methods of assembly of a medical device according to some aspects of the disclosure are now described. The medical device, in its assembled state according to some aspects of the disclosure, includes the scaffold crimped to a balloon catheter, the two piece sheath disposed over the scaffold as in FIG. 1, and the catheter being contained within a protecting tube. The aspects of the protecting tube (or coil) are discussed in greater detail below in connection with FIGS. 4A-4C, 5A-5D and 6A-6B.

The catheter assembly 2 with sheaths arranged as in FIG. 1 and contained within a protecting tube is packaged and sterilized. At the time when the catheter assembly is to be used in a medical procedure the package is opened and the tube and sheath pair removed. According to another aspect of the disclosure the catheter assembly 2 is not configured for being introduced into the patient until a sheath or sheath pair, e.g., sheath 30/230, is removed. Examples follow.

After (or before) placing the catheter within the tube, and before the sheaths 20/30 are placed, the scaffold 10 is crimped to the balloon 12 of the catheter assembly 2 using a crimping mechanism. As noted above, for a polymer scaffold the diameter reduction during crimping may be 2:1, 2.5:1, 3:1, 4:1 or higher. The scaffold may be placed on a balloon having a nominal, expanded or post-dilation diameter that is about 2, 2.5, or 3 times the diameter of the scaffold when the scaffold has a final crimp diameter on the balloon.

The diameter reduction (from a pre-crimp size to the final crimp diameter) introduces high stresses in the scaffold structure. The memory in the material following crimping causes recoil of the scaffold structure, as discussed earlier; one can incorporate lengthy dwell times within the crimper, e.g., after the final crimp step, to allow stress-relaxation to occur in the structure while heated crimper blades are maintaining a fixed diameter and temperature to facilitate stress relaxation. Both the dwell period and the imposition of a constraining sheath over the crimped scaffold after crimping helps to reduce recoil after crimping. Crimping of the scaffold 10 to the balloon 12 including desirable dwell times and temperatures that can affect stress relaxation and recoil after crimping are disclosed in U.S. patent application Ser. Nos. 12/861,719, 13/089,225 and 13/107,666.

Following removal from a crimping mechanism the scaffold will recoil unless subject to a radial constraint. According to one aspect of the disclosure a temporary one-piece sheath is placed on the scaffold immediately following crimping, then replaced by the sheath of FIG. 1 after about ½ hour from removal from the crimping mechanism. Examples of the one-piece sheath according to the disclosure is one-piece sheath 23 described in U.S. application Ser. No. 13/708,638.

The sheath pair 20/30 may be attached as follows. The sheath pair, shown in FIG. 3A, is placed on a mandrel 8 before being attached to the catheter assembly 2. The mandrel 8 is passed through the catheter shaft 4 guidewire lumen (not shown), and exits at the distal end of the catheter assembly 2. The sheath pair is then placed on the mandrel 8 distally of the catheter assembly 2. The mandrel 8 may then be used to guide the sheath pair over the scaffold-balloon 10/12 as illustrated in FIGS. 3B-3D.

Referring to FIG. 3B, the distal end 30b of the sheath 30 is adjacent to the raised end 22 of the sheath 20. In this configuration the halves 28, 29 can freely open or close. The sheath pair is then brought towards the scaffold-balloon 10/12. The halves 28, 29 easily deflect over the scaffold-balloon 10/12. The sheath pair may be slid towards the scaffold-balloon 10/12 as follows. Holding the catheter assembly 2 stationary, grasping the mandrel 8 with one hand and the sheath pair with the other hand and sliding the sheath pair over the mandrel 8 until the halves 28, 29 are located over the scaffold-balloon 10/12 as shown in FIG. 3C. When properly positioned, the portions 24, 25 are positioned with respect to proximal end 14a as shown in FIG. 1A.

Figure 3C:
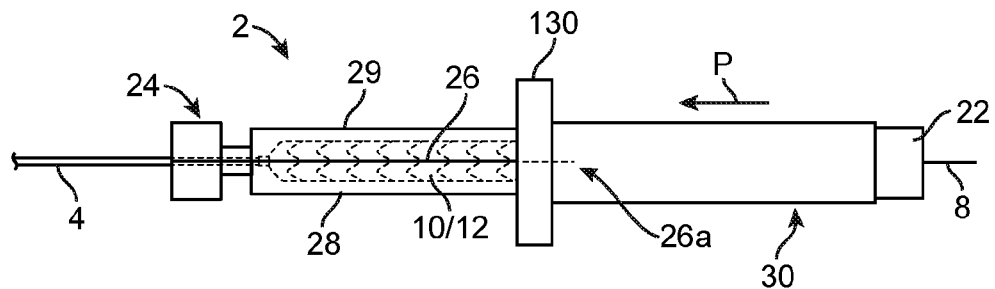
Figure 3D:
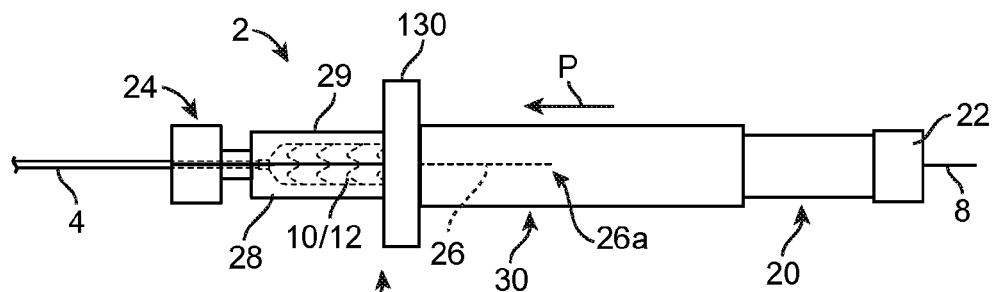

Referring to FIGS. 3C-3D, once the halves 28, 29 are located properly over the scaffold-balloon 10/12 to protect this structure, the constraining sheath 30 can be pushed over the scaffold-balloon 10/12 (as indicated in FIGS. 3C-3D by P). The sheath 30 may be pushed over the scaffold-balloon 10/12 in the following manner. The raised end 22 and mandrel 8 are grasped with one hand to hold the two stationary. Then, using the other hand the sheath 30 is pushed over the scaffold-balloon 10/12 until the end 30a of sheath 30 is disposed adjacent to, or abuts the raised end 24 of the sheath 20, which indicates the proximate location of the proximal end 14a (FIG. 1A) of the balloon-scaffold 10/12. Alternatively, the portion 24 and catheter shaft 4 may be simultaneously held with on hand, while the sheath 30 is pushed towards the scaffold 10 with the other hand. By grasping the portion 24 with the catheter shaft 4, the halves 28, 29 are held in place relative to the scaffold 10 while the sheath 30 is being pushed over the scaffold 10.

With the sheath positioned over the scaffold as in FIG. 1, the catheter is placed within a tube or coil. The tube or coil, which may be rigid compared to the catheter shaft, protects the catheter during shipment/delivery and storage. When the packaged and sterile medical device is received by a health professional, it may be enclosed within a rigid tube to protect the contents inside from damage.

According to another aspect of the disclosure, the tube or coil is fit with, or includes a member for removing a sheath or sheaths from the scaffold as the catheter is removed from the tube or coil. More generally, there is a structure including a tube and a member that interferes with a sheath constraining a scaffold when a catheter supporting the scaffold is being removed from the tube.

Referring to the example of FIG. 4A-4C, there is shown a sequence of events during removal of the catheter 2 from a tube 140. The tube has a clearance d2, which is larger than the diameter d1 of the member 130. As such, for the tube 140 having a clearance d2 everywhere long the tube's lumen, the catheter freely slides along the tube without interference from the tube. According to another aspect of the disclosure a member 152 interferes with the catheter 2 removal from the tube 140, resulting in one or more sheaths being removed from the scaffold 10 when the catheter 2 is removed from the tube 140. The member 152 (described in greater detail below) forms a reduced clearance d3, which is less than d1 and d2.

A member may be disposed near a proximal or distal end of a tube or catheter. Preferably, the member 152 is located near the catheter proximal end (i.e., adjacent the catheter hub) when the catheter is within the tube 140. Referring again to FIGS. 4A-4C, during its removal sequence the catheter 2 is withdrawn from the tube 140 proximal end (not shown) or the tube 140 pushed towards the catheter 2 distal end while the catheter proximal end is held. In either case, the member 152 is eventually is brought near the member 130 of sheath 30 and begins to push sheath 30 towards a distal end of sheath 20 or the distal end of the catheter 2. FIG. 4C shows the sheath 30 displaced to the left and almost completely removed from the scaffold 10. This action leaves only the inner sheath 20 halves 28/29 remaining over the scaffold 10. After the catheter 2 has been removed from the tube 140 the sheath 20 may be easily removed from the scaffold 10 (since sheath 20 does not apply a compressive force on the scaffold 10). In the case of a raised end 22 for sheath 20, FIG. 1, the continued movement of sheath 30 to the left in FIG. 4C by member 152 may also remove sheath 20 from scaffold 10 (as explained in greater detail in connection with FIGS. 4A-4C of U.S. Pat. No. 8,414,528). Alternatively, the sheath 20 can be partially or fully maintained in its position over the scaffold 10 after removal of the catheter from the tube 140. And the sheath 30 may be partially retained on the sheath 20 and/or the catheter after removal from the tube 140. Thus, after the catheter is removed from the tube, the sheaths 20/30 may be fully or partially removed from the scaffold 10 and/or catheter.

Embodiments of structure defining clearance d3 for interfering with a sheath are now described in connection with FIGS. 5A-5D and 6A-6B.

Referring to FIGS. 5A-5B, a clip 150 is placed near a proximal end of the tube 140. The clip may be formed by two halves 150a, 150b connected to each other through a living hinge 153. Each half 150a, 150b has a protrusion 152. The tube 140 is modified to provide two opposite through-holes 143 for passage of protrusions 152 into the bore of the tube 140 when the clip halves 150a, 150b are brought together, as illustrated in FIGS. 5A-5B. There is a clearance d3 between the ends of the protrusions 152. The clip may be held together by a fastener 156, such as adhesive, ultrasonic welding, solvent bonding, tape, cable tie or tie wrap.

Referring to FIG. 5C there is a sleeve 150' that has an inner flange 152'. The flange forms a reduced clearance d3. The inner surface of the sleeve 150' is sized to snugly receive the tube 140 so that the proximal end abuts the flange 152'. The sleeve 150' may be fastened to the proximal end of the tube 140 to provide the member in the tube 140 for interfering with the removal of the catheter 2 from the tube; that is, removing at least sheath 30 from the scaffold 10. The catheter 2, prior to crimping or prior to sheath placement, is fed into the end of sleeve 150' with tube 140 fitted at the opposite end of sleeve 150'.

Referring to FIG. 5D a rim 150" forming an inner surface 152" may be formed in the tube 140. The inner surface 152" provides a decrease in clearance from d2 to d3 near the proximal end of the tube 140. The rim 150" is formed by re-shaping an end of a tube having an inner diameter d2. Such reshaping may be accomplished by swaging or applying a combination of heat and pressure.

Figure 6A:
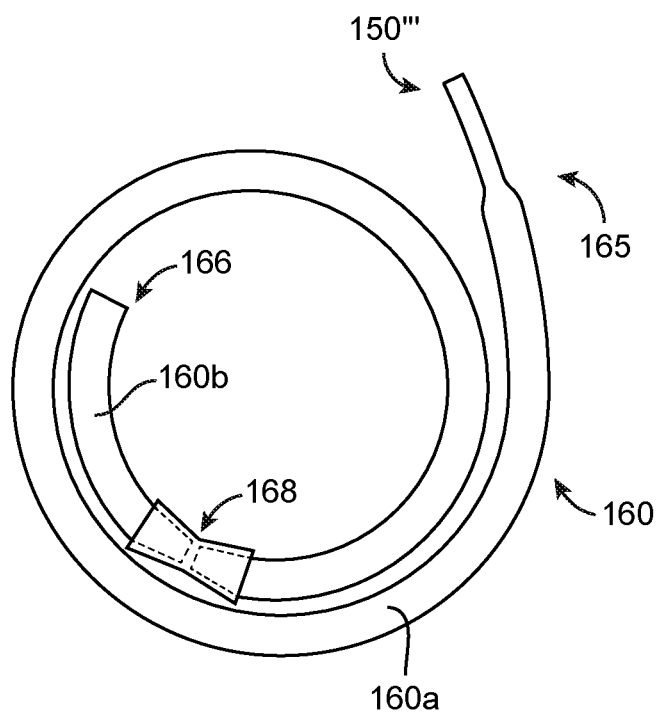
FIGS. 6A-6B depict a two-piece tube or coil having a neck formed near a proximal end of the tube.
Figure 6B:
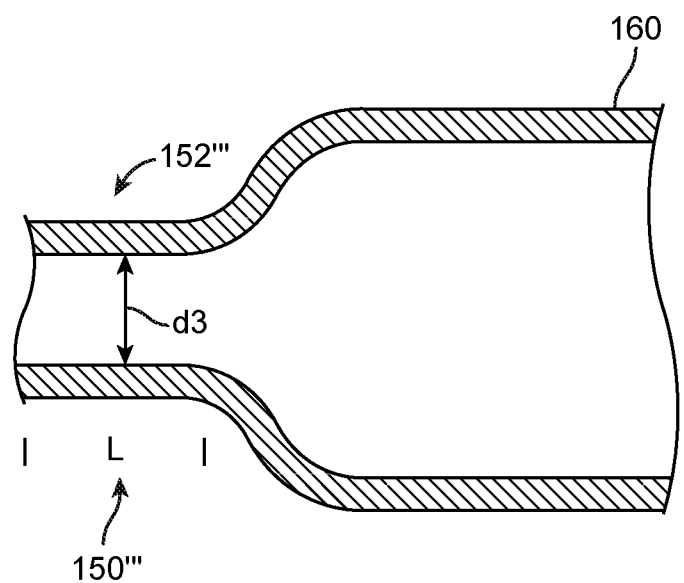

FIGS. 6A-6B depict aspects of a tube 160 for receiving the catheter 2 according to another aspect of the disclosure. In one respect the tube 160 provides another embodiment of structure forming the member for interfering with a sheath. Referring first to FIG. 6B, which refers to the proximal end 165 of the tube 160, the diameter is stepped down from d2 to d3. The d3 clearance may extend over a length L (L can be about less than or equal to the length of the sheath 30/230) to provide a narrowed passage or neck 150''' with clearance d3 between walls 152'''.

Referring to FIG. 6A the tube 160 is formed by a first tube portion 160a, which includes the proximal end 165 of the tube 160, and a second tube portion 160b, which includes the distal end 166 of the tube 160. The portions 160*a* and 160*b* are separate pieces of the tube 160. A sleeve, tape or clip 168 may be used to fasten the two pieces together. When the catheter and scaffold (radially constrained by a sheath) are assembled the catheter shaft and distal end portion are contained within the tube 160. The handle or hub portion of the catheter (not shown) is external to the tube 160 and adjacent the tube 160 proximal end 165. As indicated in FIG. 6A the neck 150''' is located near the proximal end 165. The catheter is removed from the tube 160 by pulling the handle or hub portion (e.g., the catheter portion having a steering and/or lumen pressure control) away from the tube proximal end 165 or pushing the tube towards the catheter distal end. In either case the neck 150''' interferes with a sheath, constraining sheath or outer sheath, e.g., sheath 30, but not any other portion of the catheter.

Tube 160 has a separable piece 160*b* for purposes of processing or assembly of the catheter distal end while the remaining portion of the catheter is contained within the tube portion 160*a*. The portion 160*b* of the tube 160 has a length at least equal to the length of the catheter distal portion including the balloon. With the portion 160*b* detached from the portion 160*a* an operator may have free access to the balloon 12 for crimping, inspection and/or affixing one or more sheaths to the crimped scaffold without having to remove the remainder of the catheter from the tube 160. As such, a majority of the catheter may remain within the protective tubing configured to a remove a sheath, thereby preventing inadvertent damages to the catheter shaft during processing, while a distal end including a scaffold and balloon may be inspected, a scaffold crimped to a balloon and a sheath placed over the scaffold.

The operator may place the sheath, e.g., sheath 20/30, having a member defining the d1 diameter on the crimped scaffold while the catheter remains in the tube portion 160*b*. After attaching the sheath, e.g., sheath 20/30 of FIGS. 1-2, to the scaffold, the portion 160*b* may be affixed to the portion 160*a* using the sleeve 168. If the detachable portion 160*b* were not provided, then the catheter could not be placed within the tube 160 since the neck 150''' defining clearance d3 would disrupt the constraining sheath when the catheter is placed within the tube. For a one-piece tube the structure 150, 150', 150'' or 150''' may be fitted to, formed in, or attached, respectively, to the tube after crimping and sheath placement (since the hub, handle or handle portion of the catheter is fixed at the proximal end of the shaft, the catheter shaft may only be placed within the tube from the tube proximal end 165). According to the embodiment of FIG. 6A, the neck 150''' may be formed in the tube and catheter placed within the tube 160 prior to crimping and sheath placement. After sheath placement the portion 160*b* can be re-attached.

With reference to FIGS. 7A-7D and FIGS. 8A-8C, now described are sheaths according to other aspects of the disclosure.

Figure 7A:
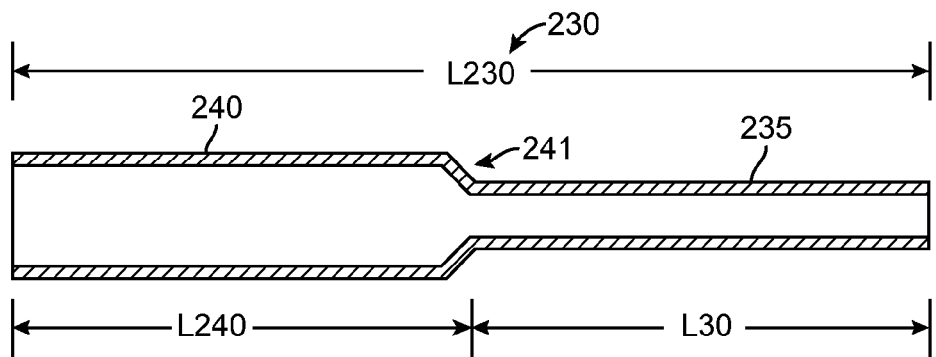
FIGS. 7A-7D depict aspects of a second and third pair of sheaths for constraining and protecting a scaffold.
Figure 7B:
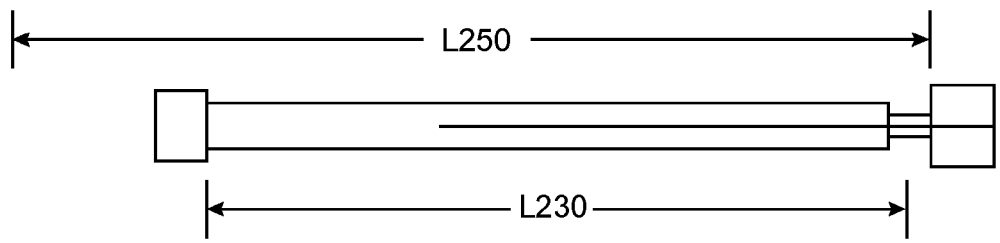
Figure 7C:
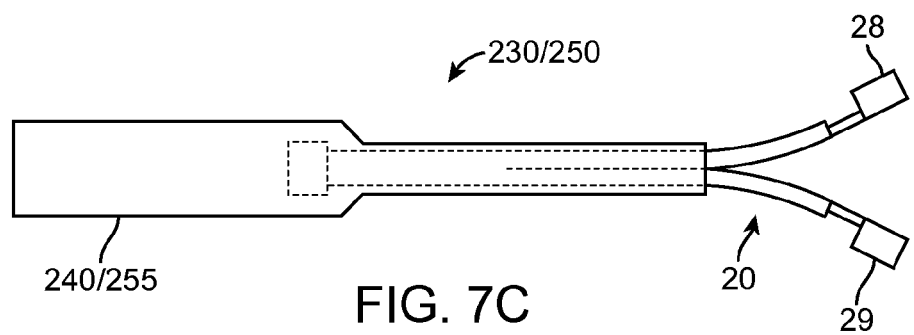

Referring to FIGS. 7A-7C, as an alternative to sheath 20/30 depicted in FIGS. 1-2 and described earlier, a modified sheath 230 replaces the sheath 30. Sheath 230 differs from sheath 30 in the following manner. Sheath 230 does not include the member 130 and sheath has an expanded portion that may be gripped by a user without also pulling on the protecting sheath 20 during sheath removal. The sheath 20/230 (FIGS. 7A-7B) facilitates a more safe removal of the constraining sheath by preventing, prior to, or current with, removal of the sheath 230 the protecting sheath 20. Removing both sheaths at the same time can damage the scaffold or catheter, as discussed above. The preferred removal is to remove sheath 20 only after a constraining sheath 230 has cleared the scaffold.

By providing the extension 240 having a length L240 (as opposed to sheath 30 having a total length L30) a user is discouraged from gripping the sheath 20, since the extension 240 is disposed over about the entirety of sheath 20 (thereby making it difficult to pull on sheath 20 directly). The sheath 230 includes a portion 240 and 235. The portion 240 may have a larger outer diameter than the portion 235. The sheath 230 may be formed from a single tube with diameter of the portion 240. The portion 235 is formed as stepped-down part of the tube 230 and has length L30. The portion 235 applies the radially compressive force on the scaffold 10. The total length of the sheath 230 is L230, which is equal to the sum of L30 and L240. The length L230 may be about or slightly less than the length of sheath 20, such that both ends 24 and 22 of sheath 20 are visible when sheath 230 is disposed over sheath 20.

Figure 8A:
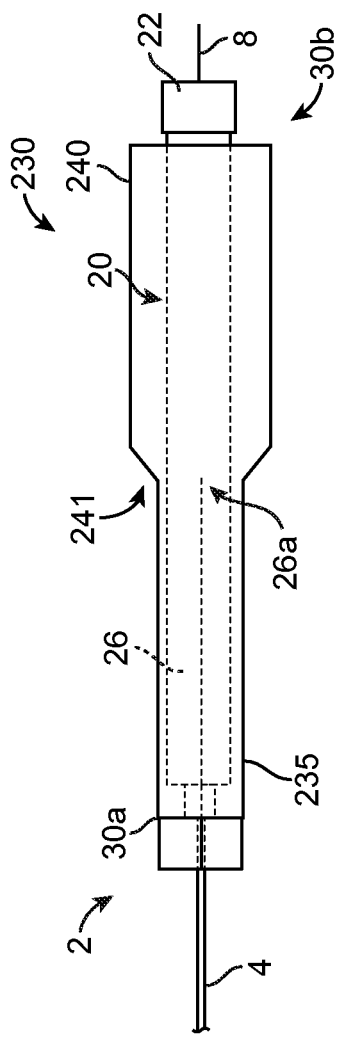
FIGS. 8A-8C show a sequence for removal of the sheath pairs of FIGS. 7A-7D.

A method of removal of the sheath 20/230 from the scaffold 10 is now described. At the time when the catheter assembly is to be used in a medical procedure the package is opened and the sheath pair removed from the distal end. The catheter assembly 2 is not configured for being introduced into the patient until the sheath pair is removed. FIG. 8A depicts the arrangement of the sheaths 20, 230 at the distal end of the catheter assembly 2 when the packaged and sterile medical device is received by a health professional. Examples of such sterile packaging is found in U.S. patent publication no. US 2008-0010947. The sheath 20 and portion 240 may extend well-beyond the distal end of the catheter 2 assembly such that they overhang the catheter distal end by about the length of the scaffold or length L30. These overhanging portions are provided to facilitate an intuitive removal of the sheath pair by a health professional, thereby reducing the chances that the sheath pair are removed improperly.

Figure 8B:
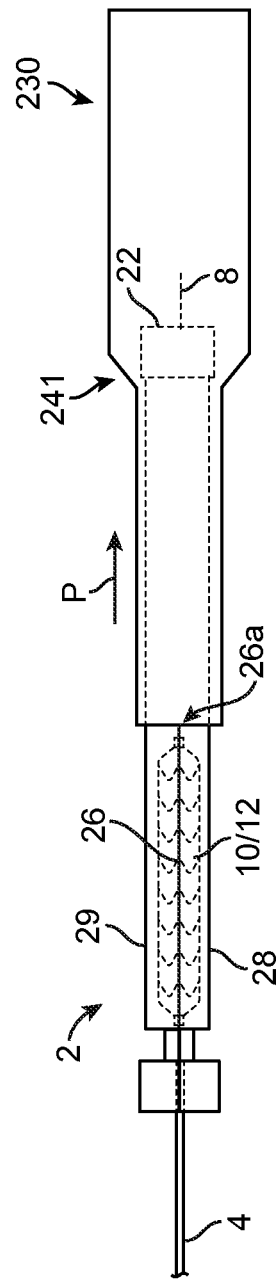
Figure 8C:
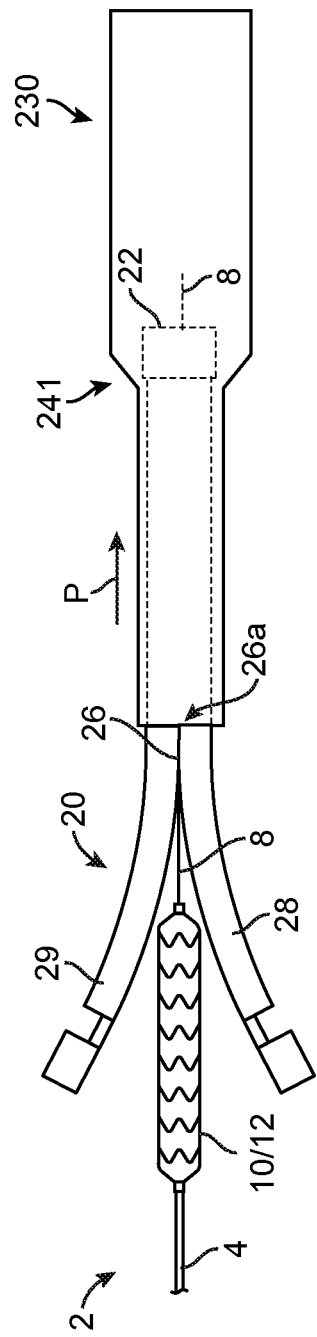

Referring to FIGS. 8A-8C, methods for removing the sheath pair from the scaffold-balloon 10/12 by the health professional are now described. These illustrations refer to moving the sheath pair over the mandrel 8; however, a mandrel 8 is not necessary. The sheath pair 30/230 may be safely removed from the catheter assembly 2 without using a mandrel 8.

A sterilized and packaged catheter assembly with sheaths 20, 230 positioned as shown in FIG. 8A typically includes the stiffening or storage mandrel 8 in the catheter shaft 4 lumen to provide bending stiffness for shaft 4. A distal end of the mandrel 8 has a curled end, or an extension/stop at the distal end (not shown), which is used to manually withdraw the mandrel 8 from the catheter shaft 4 lumen by pulling the mandrel 8 towards the distal end 6 of the catheter assembly 2. In the following example the sheaths 20, 230 are removed. The proscribed steps preferably also include the act of removing the mandrel 8 from the catheter shaft lumen by, e.g., simultaneously gripping the raised end 22, sheath 230 and mandrel 8.

First, the sheath 230 portion 240 is grabbed and pulled away from the scaffold-balloon 10/12 structure, which removes the constraining portion 235 from the scaffold-balloon 10/12 structure. The sheath 230 may be withdrawn or pulled away from the scaffold-balloon 10/12 in the following manner. One hand grasps the portion 230; the other hand grasps the catheter shaft 4 proximal of the scaffold 10 to hold the catheter 2 stationary. The sheath 230 is pulled in the direction P (FIG. 8B). When the ID junction 241 abuts the stepped end 22 of sheath 20, the constraining portion 235 has cleared the scaffold. At this point continued pulling of the sheath 230 will also remove the sheath 20 from the scaffold and eventually separate the sheath 20/230 from the catheter 2. The raised end 22 therefore functions as an abutment for removing both sheaths in a safe manner with minimal disruption to the crimped scaffold.

Figure 7D:
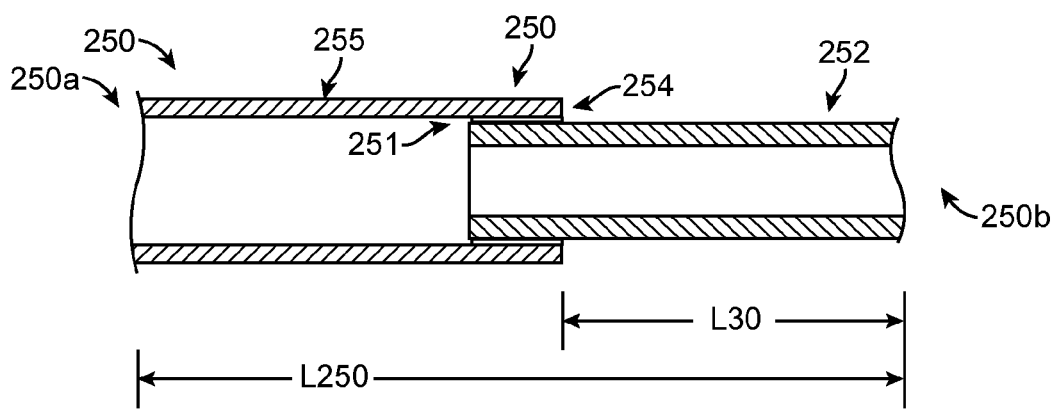

As an alternative to the sheath 230 formed from a single piece of tubing, in FIG. 7D there is a sheath 250 made from two tubes of different diameter fastened together. A sheath 250 has a first portion 252 that applies the radial constraint to the scaffold and a second portion 255 for removal of the first portion 252 from the scaffold. The sheath 250 may be positioned and removed from the sheath 20 in the same manner as described above for sheath 230. As with sheath 230 there is the ID junction 251 for abutment with the end 22 when the sheath 250 is removed.

In a preferred method of making sheath 20, the raised ends are made with the sheath 30 and 230 over the tube forming the sheath 20. The raised ends retain the sheath 30 on the sheath 20. Since the one-piece sheath 30/230 is disposed over the tube forming the sheath 20 prior to forming the raised ends, the overall length of the one-piece sheath 30/230 is preferably limited to less than the overall length of the sheath 20 (so that for manufacturing reasons the ends can be accessed to form the raised ends). However, by using a two-piece sheath 250 the overall length L250 of the finished sheath can be significantly longer than the sheath 20, since the raised ends of sheath 20 can be formed with the portion 252 on sheath 20 but prior to the tube portion 255 attached at 254 (FIG. 7D). According to the embodiment of FIG. 7D the sheath 250 may preferably either have a longer length L250 than sheath 20 length, a length about the same as sheath 20 or shorter length.

According to a method of crimping, a crimping process at or near to a glass transition temperature of the polymer of the scaffold 10 is conducted as explained in U.S. application Ser. No. 13/644,347 including FIGS. 3A and 4A. Before placing a two-piece sheath as described above, a temporary sheath may be formed with slits or weakened areas that will facilitate a tearing away of the sheath when it is attached to the scaffold. Examples of such a sheath is described in U.S. application Ser. No. 13/708,638 as shown in FIGS. 2, 3A-3E and 4.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. An apparatus, comprising:
    a catheter including a scaffold comprising a polymer, the scaffold being crimped to a balloon;
    a sheath disposed over the scaffold;
    a tube containing at least a portion of the catheter, wherein walls of a lumen of the tube define a first clearance that permits the catheter to slide within the tube without interference from the lumen walls; and
    a clip, rim or flange attached to the tube and located adjacent the lumen walls, or a tube portion, wherein the clip, rim, flange, or tube portion defines a second clearance, less than the first clearance and partially or fully interferes with the sheath when the catheter slides within the tube and relative to the clip, rim, flange or tube portion;
    wherein the catheter is configured for being introduced into a mammalian body only after the sheath is removed from the scaffold.

2. The apparatus of claim 1, wherein the scaffold is formed from a radially expanded tube having a pre-crimp diameter that is at least about 1.5 times, at least about 2 times, at least about 3 times, or at least about 4 times a crimped diameter of the scaffold.

3. The apparatus of claim 1, wherein the clip, rim, flange, or tube portion is disposed at an end of the catheter or the tube.

4. The apparatus of claim 1, wherein the tube is rigid compared to the sheath.

5. The apparatus of claim 1, wherein the tube extends substantially the entire length of a shaft of the catheter, whereby a majority of the catheter is contained within the tube.

6. The apparatus of claim 5, wherein a proximal end of the tube is adjacent a hub or handle portion of the catheter.

7. The apparatus of claim 1, wherein the sheath includes a constraining portion and a protecting portion, the constraining portion applying a radial inward force on the crimped scaffold to limit recoil of the scaffold.

8. The apparatus of claim 7, wherein the sheath is a two piece sheath.

9. The apparatus of claim 1, wherein the sheath includes a raised portion that abuts the clip, rim, flange, or tube portion when the catheter slides within the tube, thereby causing the sheath to become fully or partially removed from the scaffold.

10. The apparatus of claim 1, wherein the sheath has a first and second portion having respective first and second outer diameters, the first outer diameter being larger than the second outer diameter, wherein the sheath is fully or partially removed from the scaffold when the first portion abuts the clip, rim, flange, or tube portion.

11. The apparatus of claim 1, wherein the tube further comprises a first tube portion connected to a second tube portion,
    wherein an end of the first tube portion is adjacent a hub or handle portion of the catheter,
    wherein the second tube portion has a length at least equal to a length of the balloon, and
    the second tube portion is connected to the first tube portion.

12. An apparatus for delivery of a medical device, comprising:
    a balloon catheter including a shaft, a hub and a balloon having a nominal inflation diameter;
    a scaffold formed from a tube comprising a polymer;
    the scaffold being crimped to the balloon and having a crimped diameter, wherein the balloon nominal inflation diameter is about 2, about 3 or about 4 times greater than the crimped diameter of the scaffold;
    a protecting sheath disposed over the scaffold;
    a constraining sheath disposed over the protecting sheath and the scaffold; and a rigid tube containing the catheter, wherein a majority of the catheter is contained within the tube;

the rigid tube further including a clip, rim, or flange attached to the rigid tube and located adjacent the lumen walls, or a tube portion, wherein the clip, rim, flange, or tube portion partially or fully interferes with the constraining sheath when the catheter slides within the rigid tube and relative to the clip, rim, or flange or tube portion wherein the catheter is adapted for being passed through a mammalian body only after the catheter is removed from the rigid tube and the protecting sheath and constraining sheath are removed from the catheter.

13. The apparatus of claim 12, wherein the tube comprising the polymer is an expanded polymer tube having a morphology characterized by substantially radially aligned polymer chains resulting from a biaxial expansion of a precursor tube in the radial direction by between about 200% to about 450%, and wherein the scaffold diameter prior to crimping is at least 2-3 times higher than the crimped diameter.

14. The apparatus of claim 13, wherein the scaffold is made from a polymer composition comprising PLLA.

15. The device of claim 12, wherein the tube comprising the polymer is an expanded tube and wherein the expanded tube is made from a precursor tube that was expanded in a radial direction by about 400% to 450% and in an axial direction by between 150% and 200% or between 10% and 50%.

16. The apparatus of claim 12, wherein the tube is configured to partially or fully remove the constraining sheath from the scaffold, or partially or fully remove the constraining sheath from the catheter when the catheter is withdrawn from an end the tube.

17. The apparatus of claim 12, wherein the scaffold is formed from a tube having a pre-crimp diameter that is at least about 3 times a diameter of the crimped scaffold.

18. An apparatus, comprising:
a catheter including a scaffold comprising a polymer, the scaffold being crimped to a balloon;
a sheath disposed over the scaffold;
a tube containing at least a portion of the catheter and comprising means for partially or fully removing the sheath from the scaffold when the catheter slides within the tube;
wherein the catheter is configured for being introduced into a mammalian body only after the sheath is removed from the scaffold.

19. The apparatus of claim 18, wherein a majority of the catheter is contained within the tube.

20. The apparatus of claim 18, wherein the scaffold is formed from a tube having a pre-crimp diameter that is at least about 3 times a diameter of the scaffold.

* * * * *